United States Patent
Leaf et al.

(10) Patent No.: US 7,459,294 B2
(45) Date of Patent: Dec. 2, 2008

(54) METHOD OF PRODUCING A COMPOUND BY FERMENTATION

(75) Inventors: Timothy A. Leaf, Newark, CA (US);
Ruchir P. Desai, Foster City, CA (US);
Peter Licari, Fremont, CA (US); Elaine Jennifer Woo, Jackson, FL (US)

(73) Assignee: Kosan Biosciences Incorporated, Hayward, CA (US)

( * ) Notice: Subject to any disclaimer, the term of this patent is extended or adjusted under 35 U.S.C. 154(b) by 230 days.

(21) Appl. No.: 10/913,180

(22) Filed: Aug. 6, 2004

(65) Prior Publication Data

US 2005/0130283 A1    Jun. 16, 2005

Related U.S. Application Data

(60) Provisional application No. 60/493,959, filed on Aug. 8, 2003.

(51) Int. Cl.
| | |
|---|---|
| C12P 19/44 | (2006.01) |
| C12P 19/60 | (2006.01) |
| C12P 19/62 | (2006.01) |
| C12P 17/00 | (2006.01) |
| C12P 17/02 | (2006.01) |

(52) U.S. Cl. ............... 435/74; 435/75; 435/76; 435/117; 435/123; 435/252.3; 435/252.33; 435/252.35

(58) Field of Classification Search ............ None
See application file for complete search history.

(56) References Cited

U.S. PATENT DOCUMENTS

| | | | |
|---|---|---|---|
| 5,624,814 A | 4/1997 | Waters et al. | |
| 6,033,883 A | 3/2000 | Barr et al. | |
| 6,063,561 A * | 5/2000 | Katz et al. ............ | 435/4 |
| 6,066,721 A | 5/2000 | Khosla et al. | |
| 6,080,555 A | 6/2000 | Khosla et al. | |
| 6,117,670 A | 9/2000 | Ligon et al. | |
| 6,177,262 B1 | 1/2001 | Ziermann et al. | |
| 6,200,813 B1 * | 3/2001 | Katz et al. ............ | 435/477 |
| 6,221,641 B1 | 4/2001 | Khosla et al. | |
| 6,242,211 B1 | 6/2001 | Peterson et al. | |
| 6,258,566 B1 * | 7/2001 | Barr et al. ............ | 435/76 |
| 6,271,255 B1 | 8/2001 | Leadlay et al. | |
| 6,391,594 B1 * | 5/2002 | Khosla et al. ........... | 435/91.4 |
| 6,403,775 B1 | 6/2002 | McDaniel | |
| 6,410,301 B1 | 6/2002 | Julien et al. | |
| 6,492,562 B1 | 12/2002 | Ashley et al. | |
| 6,500,960 B1 | 12/2002 | Khosla et al. | |
| 6,514,944 B2 | 2/2003 | Chu | |
| 2002/0045609 A1 | 4/2002 | Ashley et al. | |
| 2002/0052028 A1 | 5/2002 | Santi et al. | |
| 2002/0119937 A1 | 8/2002 | Khosla et al. | |
| 2002/0137152 A1 | 9/2002 | Santi et al. | |
| 2003/0023082 A1 | 1/2003 | Ashley et al. | |
| 2003/0073205 A1 * | 4/2003 | Arslanian et al. ........... | 435/117 |
| 2003/0077707 A1 * | 4/2003 | Khosla et al. ............ | 435/69.1 |
| 2003/0077760 A1 * | 4/2003 | Khosla et al. ............ | 435/91.2 |
| 2003/0096374 A1 | 5/2003 | Ashley et al. | |
| 2004/0014183 A1 | 1/2004 | Licari et al. | |
| 2004/0146992 A1 | 7/2004 | Regentin et al. | |

FOREIGN PATENT DOCUMENTS

| | | |
|---|---|---|
| EP | 0546819 A1 | 6/1993 |
| WO | WO 98/41869 A1 | 9/1998 |
| WO | WO 01/83803 A1 | 11/2001 |
| WO | WO 02/32916 A2 | 4/2002 |

OTHER PUBLICATIONS

Gerth et al., *J. Antibiotics* 47 (1), 23-31 (1994), "The Soraphens: A Family of Novel Antifungal Compounds from *Sorangium celluosum*-(Myxobacteria)".

Jarvis et al., *J. Antibiotics* 43 (11), 1502-1504 (1990), "Use of Resins for Trichothecene Production in Liquid Cultures".

Khosla, *Chem. Rev.* 97, 2577-2590 (1997), "Harnessing the Biosynthetic Potential of Modular Polyketide Synthases".

Leaf et al., *J. Chem. Technol. Biotechnol.* 77, 1122-1126 (2002), "Employing racemic precursors in directed biosynthesis of 6-dEB analogs".

Marshall et al., *J. Ind. Microbiology* 5, 283-288 (1990), "The effect of neutral resins on the fermentation production of rubradirin".

Mitsubishi Chemicals, product information on Diaion and Sepabeads resins, from website www.diaion.com (accessed Oct. 24, 2004).

(Continued)

*Primary Examiner*—Herbert J. Lilling
(74) *Attorney, Agent, or Firm*—Anastasia P. Winslow (57) ABSTRACT

During the production of a product compound by fermentation, the concentration of a precursor compound is maintained within a pre-selected concentration range by having an adsorbent resin in contact with the culture medium. The adsorbent resin reversibly adsorbs precursor compound and, as un-adsorbed precursor compound is converted to product compound, adsorbed precursor compound is released from the resin, thus maintaining the concentration of precursor compound within the pre-selected range.

12 Claims, 4 Drawing Sheets

OTHER PUBLICATIONS

Pacey et al., *J. Antibiotics* 51 (11), 1029-1034 (1998), "Novel Erythromycins from a Recombinant *Saccharopolyspora erythraea* Strain NRRL 2338 pIGI I. Fermentation, Isolation and Biological Activity".

Rohm and Haas Product Data Sheet, "Amberchrom® CG161" (Sep. 2002).

Rohm and Haas Product Data Sheet, "Amberlite® XAD16" (Oct. 2003).

Warr et al., *J. Antibiotics* 49, 234-240 (1996), "BMS-182123, a Fungal Metabolite that Inhibits the Production of TNF-α by Macrophages and Monocytes".

* cited by examiner

Fig. 1

Concentration of Pr-SNPC (■)

Supernatant concentration of 15-Me-6-dEB (○)

Whole broth extraction of 15-Me-6-dEB (●)

Fig. 2

Comparative strain JRJ2* (O)
Strain B9 in resin-free fermentation (□)
Strain B9 in resin-containing fermentation (■)

Fig. 3

Pr-SNPC concentration (● soluble, □ bound)

Fig. 4

Super-saturation study of 15-Me-6-dEB.

15-Me-6-dEB concentrations in supernatant measured after

1 day (■ in acetonitrile, ● in water)

11 days (□ in acetonitrile, ○ in water)

METHOD OF PRODUCING A COMPOUND BY FERMENTATION

CROSS-REFERENCE TO RELATED APPLICATIONS

This application claims the benefit of U.S. Provisional Application No. 60/493,959, filed Aug. 8, 2003; the disclosure of which is incorporated herein by reference.

BACKGROUND OF THE INVENTION

1. Field of the Invention

This invention relates to a method of producing a compound by fermentation.

2. Description of Related Art

The traditional organic chemical synthesis of industrial quantities of a structurally complex natural product or an analog thereof is often inefficient because of the product's structural complexity. An alternative is biosynthesis, via the fermentation of a culture of an organism capable of producing the product. Where the product is not a natural product, a genetically modified organism may be used. In either case, the product must be isolated from the culture medium and the producing organism at the conclusion of a fermentation run. A common isolation technique is to contact the fermentation broth with a resin that adsorbs the product. The contacting may be accomplished by passing the broth through a chromatography column loaded with the resin or by adding the resin to the broth and stirring. The resin and broth are separated, after which the product is isolated by elution from the resin. As most products are hydrophobic molecules, hydrophobic (unfunctionalized) resins are preferred. See, for example, Ashley et al., U.S. Pat. No. 6,492,562 B1 (2002); Chu, U.S. Pat. No. 6,514,944 B2 (2003); Ashley et al., US 2002/0045609 A1 (2002); Santi et al., US 2002/0052028 A1 (2002); Santi et al., US 2002/0137152 A1 (2002); Ashley et al., US 2003/0023082 A1 (2003); and Ashley et al., US 2003/0096374 A1 (2003); the disclosures of which are incorporated herein by reference.

In a variation of the above technique, the resin is present during the fermentation run, either ab initio (i.e., at the time of seeding) or starting partway through it. The resin's presence has been reported to improve production levels and, where the product is unstable, to sequester it and prevent its degradation. See, for example, Ligon et al., U.S. Pat. No. 6,117,670 (2000); Peterson et al., U.S. Pat. No. 6,242,211 B1 (2001); McDaniel, U.S. Pat. No. 6,403,775 B1 (2002); Khosla et al., US 2002/0119937 A1 (2002); Khosla et al., US 2003/0077760 A1 (2003); Nasby et al., WO 98/41869 (1998); Yamazaki et al., EP 0,546,819 A1 (1993); Marshall et al., *J. Ind. Microbiology* 5,283-288 (1990); Jarvis et al., *J. Antibiotics* 43 (11), 1502-1504 (1990); Gerth et al., *J. Antibiotics* 47 (1), 23-31 (1994); and Warr et al., *J. Antibiotics* 49, 234-240 (1996); the disclosures of which are incorporated herein by reference.

A resin's presence can also control the distribution of a product mixture. For instance, in the production of epothilones by fermentation of recombinant *Myxococcus* host cells, epothilones A and B are produced when resin is absent but epothilones C and D are produced when resin is present. See Julien et al., U.S. Pat. No. 6,410,301 B1 (2002) and Arslanian et al., US 2003/0073205 A1 (2003); the disclosures of which are incorporated by reference.

When a patient's bodily fluid sample is cultured to identify and isolate an infecting microorganism that might be present, antibiotics previously administered to the patient can interfere with the culturing process. The addition to the culture medium of a resin to adsorb and isolate the interfering chemicals is taught in Waters et al., U.S. Pat. No. 5,624,814 (1997), the disclosure of which is incorporated herein by reference.

BRIEF SUMMARY OF THE INVENTION

We have discovered that an adsorbing resin can be used in a fermentation process in yet another way, to manipulate the concentration of starting material and thus improve the process. Accordingly, this invention provides a method of making a product compound by culturing, in a culture medium containing a precursor compound, a producing organism that converts the precursor compound to the product compound, comprising the steps of:

(a) selecting a target concentration range for said precursor compound in said culture medium; and (b) culturing said producing organism in said culture medium to produce said product compound, said culture medium being in contact with a resin that reversibly binds said precursor compound so that the concentration of unadsorbed precursor compound in said culture medium is maintained within the target concentration range by the release of said precursor compound bound to the resin as said precursor compound is converted to the product compound.

There are a number of advantages to holding the concentration of the precursor compound within a pre-selected range in this manner. The producing organism's productivity may be sensitive to the concentration of precursor compound. Where the fermentation run extends over several days, periodic monitoring of precursor compound concentration and feeding is rendered unnecessary. If the precursor compound has limited stability in solution, its sequestration onto the resin helps stabilize it.

DETAILED DESCRIPTION OF THE INVENTION

In a preferred embodiment of the invention, the biosynthesized compound is a polyketide. The polyketides are a diverse family of compounds that have utility as antibacterial agents (erythromycin A, spiramycin), antifungal agents (amphotericin B), immunosuppressants (rapamycin, FK506), and anti-cancer agents (doxorubicin), among other applications. Polyketides are biosynthesized from two-carbon units in a series of Claisen condensations in which the initially formed product at each condensation step is a β-keto ester ("ketide," hence the name "polyketide").

The enzymes (polyketide synthases, or PKSs) responsible for the biosynthesis of many polyketides are organized in a modular fashion. PKSs of the modular type are referred to as the Type I PKSs to distinguish them from other types of PKSs. Hereinafter in this specification a reference to "PKS" means a Type I PKS unless indicated otherwise.

PKSs are large multifunctional enzymes divided into modules of activity operating in assembly-line fashion, the modules being located between a loading domain and a release domain. The loading domain initiates polyketide synthesis by loading a "starter unit" (an activated small carboxylic acid) onto the PKS. The loading domain transfers the starter unit to the first module, where a two-carbon extender unit condenses with it. The first module then passes the growing polyketide chain to the second module for the addition of a further extender unit, and so forth. Each module has a number of domains (enzymatic activities) that load, activate, and condense the extender unit to the growing polyketide chain and can further have β-keto modifying domains that perform chemical modifications (e.g., reduction, dehydration) on the β-keto group. The number and order of modules, their extender unit specificity, and the types (if any) of their modifying domains determine the structure of the resulting polyketide product. Lastly the release domain frees the finished polyketide chain from the PKS. The term "thioesterase domain" has been used more or less synonymously with release domain, because the growing polyketide chain is attached to the PKS as a thioester and many release domains cleave the thioester bond and cyclize the newly liberated carboxyl group with a hydroxyl group located along the polyketide chain to form a macrolactone. Other enzymes may further modify the macrolactone, e.g., by glycosylation or cytochrome P450 monooxygenase-mediated oxidation, in what are referred to as post-PKS steps.

This modular arrangement makes Type I PKSs attractive candidates for genetic engineering. Type I PKS domains are separated by linker regions that define the boundaries of each domain. The product synthesized by a PKS can be altered (usually at the level of encoding DNA) by replacing a domain with a domain of different specificity from another PKS or by changing the activity of or inactivating a β-keto modifying domain. Expression of the altered PKS gene in a host cell produces an analog of a naturally occurring polyketide, i.e., a compound that is structurally related to but different from the naturally occurring polyketide, sometimes referred to as an "unnatural" natural product. Even where a PKS is used to produce a naturally occurring compound, expression of the PKS genes in a recombinant host organism may be preferable for one reason or another (higher yield, ease of culture, non-production of interfering metabolites, etc.). For a review on PKS structure, mechanism of action, and bioengineering, see Khosla, *Chem. Rev.* 1997, 87, 2577-2590, the disclosure of which is incorporated herein by reference.

The producing organism preferably is a microorganism, more preferably a microorganism that produces a polyketide as the product compound. The producing organism can be either a natural producer or one that is not a natural producer but has been genetically engineered to produce the product compound. It can be a bacterium (especially mycelial bacterium such as actinomycetes), a yeast, or a fungus. Suitable producing organisms are disclosed in Barr et al., U.S. Pat. No. 6,033,883 (2001); Katz et al., U.S. Pat. No. 6,063,561 (2000); Julien et al., U.S. Pat. No. 6,410,301 B1 (2002); Ziermann et al., U.S. Pat. No. 6,177,262 (2001); Leadley et al., U.S. Pat. No. 6,271,255 B1 (2001); McDaniel, U.S. Pat. No. 6,403,775 B1 (2002); Khosla et al., US 2002/0119937 A1 (2002); Santi et al., WO 01/83803 A1 (2001); Katz et al., WO 02/32916 A2 (2002); Yamazaki et al., EP 0,546,819 A1 (1993); Marshall et al., *J. Ind. Microbiology* 5,283-288 (1990); Jarvis et al., *J. Antibiotics* 43 (11), 1502-1504 (1990); Gerth et al., *J. Antibiotics* 47 (1), 23-31 (1994); and Warr et al., *J. Antibiotics* 49, 234-240 (1996); the disclosures of which are incorporated herein by reference. Producing organisms that can be used in this invention include but are not limited to *Streptomyces lividans, Streptomyces coelicolor, Saccharopolyspora erythraea, Streptomyces venezuelae, Streptomyces narbonensis, Streptomyces fradiae, Streptomyces thermotolerans, Micromonospora megalomicea, Saccharomyces cerevisiae, Escherichia coli, Myxococcus xanthus, Streptomyces hygroscopicus, Streptomyces antibioticus, Streptomyces avermitilis, Sorangium cellulosum, Streptomyces platensis, Mycothecium verrucaria, Penicillium chrysogenum,* and *Streptomyces spectabilis*. Preferred producing organisms are *Streptomyces lividans, Streptomyces coelicolor, Saccharopolyspora erythraea, Streptomyces fradiae, Saccharomyces cervisiae, Escherichia coli,* and *Myxococcus xanthus.*

Where it is stated herein that the precursor compound is converted to the product compound, this does not mean that product compound is necessarily exclusively derived from the precursor compound. The product compound may include molecular portions derived from other chemicals in the culture medium, whose target concentrations are not regulated in the manner of this invention because there is no need for doing so. An example of a product compound that is not exclusively derived from the precursor compound is a polyketide, where one of the ketide units (either the starter unit or one of the extender units) is the precursor compound and the remaining ketide units are derived from other sources.

The precursor compound preferably is one that the producing organism is incapable of biosynthesizing for itself and that therefore must be added to, or "fed," to the culture medium. Such a situation is likely to arise in the instance of a producing organism that is not a natural producer of the product compound, but which has been genetically engineered to do so. It is often not feasible or practical to transform the producing organism with not just set of genes needed to produce the product compound, but also all the genes necessary for the production of all precursor compounds. If the transformed producing organism's native genome does not include the genes for the biosynthesis of the precursor compound, then the precursor compound must be supplied by feeding. Exemplary disclosures relating to the feeding of precursor compounds include Katz et al., U.S. Pat. No. 6,063,561 (2000); Leadley et al., U.S. Pat. No. 6,271,255 B1 (2001); and Pacey et al., *J. Antibiotics* 51 (11), 1029-1034 (1998); the disclosures of which are incorporated herein by reference.

In another embodiment, the producing organism is transformed with a PKS modified so that the PKS is unable to use the native starter unit but instead accepts a diketide as an alternative "starter unit." See Khosla et al., U.S. Pat. No. 6,066,721 (2000); U.S. Pat. No. 6,080,555 (2000); and U.S. Pat. No. 6,500,960 B1(2002), the disclosures of which are incorporated herein by reference. In yet another embodiment involving polyketide synthesis, the precursor compound is a non-natural extender unit such as methylmalonyl N-acetyl cysteamine thioester, as disclosed in Khosla et al., U.S. Pat. No. 6,221,641 B1 (2001), the disclosure of which is incorporated herein by reference. The foregoing techniques—referred to as "precursor directed biosynthesis"—allow the biosynthesis of analogs of naturally occurring compounds by changing the structure of the precursor fed to the producing organism. Precursor directed biosynthesis is a particularly attractive method of making analogs of 6-deoxyerythronolide B ("6-dEB"), an intermediate in the biosynthesis of the erythromycin antibiotics.

6-Deoxyerythronolide B (6-dEB)

There are two reasons for the interest in 6-dEB analogs. First, the 6-dEB PKS (6-deoxyerythronolide B synthase, or "DEBS") has been extensively studied and the feasibility of replacing or altering various domains therein has been demonstrated. Second, analogs based on the erythromycin molecular scaffold have interesting biological properties, ranging from new antibiotics to motilides.

The target concentration range of the precursor compound preferably is between 0.01 g/L and 5.00 g/L, more preferably between 0.05 and 4 g/L, and most preferably between 0.5 and 3 g/L. The target concentration may be recorded on a tangible data storage medium, preferably before the commencement of the fermentation process. The tangible storage medium can be a paper (as in a written, typed, or printed document), magnetic (as in a disk driving or magnetic tape), optical (as in a CD), or electronic (as in memory chips).

Those skilled in the art will appreciate that there may be an independent advantage to the presence of the resin, apart from sequestration of the precursor compound. Often, the product compound is a hydrophobic compound that is itself also adsorbed onto the rein, resulting in its sequestration. The sequestration of the product compound is potentially advantageous in a number of respects. Its isolation is simplified, requiring only the physical separation of the resin from the culture medium and the producing organism after fermentation (e.g., by filtration or decantation), followed by elution. If the product compound is sparingly soluble in the culture medium, it may precipitate out when its concentration exceeds a threshold level and interfere with continued production. Even where solubility is not a factor, continued production may be inhibited by an elevated concentration of product compound. Or, the product compound may be unstable and susceptible to degradation unless sequestered onto the resin. Lastly, in the specific context of the present invention, if the product compound and the precursor compound bind competetively to the resin, binding of the product compound can drive more of the adsorbed precursor compound into solution, resulting in its more complete utilization.

The resin preferably comprises a non-ionic (unfunctionalized), hydrophobic polymer, such as a polystyrene or a styrene-divinylbenzene copolymer. Such resins are highly porous and can reversibly adsorb organic molecules from an aqueous medium. Exemplary suitable resins include the Amberlite™ XAD resins (particularly grades XAD16, XAD16HP, XAD7, XAD8, XAD1180, and XAD5), Amberchrom™ resins (particularly grade CG161), the DIAION™ resins (particularly grade HP20) and the SEPABEADS™ resins. Amberlite™ and Amberchrom™ resins are available from Rohm & Haas while the DIAION™ and the SEPABEADS™ resins are available from Mitsubishi Chemical. The resin preferably is present in an amount ranging from 1 to 120 g per liter of culture medium and preferably from 5 to 100 g/L. Those skilled in the art will appreciate that it may be desirable to empirically determine the desired type and amount resin taking into consideration the structure of the product compound, the type of culture medium, the producing organism, and related variables.

The practice of this invention can be further understood by reference to the following examples, which are provided by way of illustration and not of limitation. While following examples relate specifically to the biosynthesis of a specific compound, the skilled artisan will appreciate that the principles illustrated are applicable to the biosynthesis of other compounds.

EXAMPLE 1

General

Precursor-directed biosynthesis was employed to make a 13-substituted 6-dEB analog, namely 15-methyl-6-deoxy-erythronolide B ("15-Me-6-dEB"), using an improved strain of *Streptomyces coelicolor*.

15-Me-6-dEB

EXAMPLE 2

*S. coelicolor* Strain

We took several *Streptomyces coelicolor* that expressed heterologous DEBS genes and were capable of biosynthesis of 6-dEB or 6-dEB analogs. The strains were subjected to mutagenesis (nitrosoguanidine, UV light, or ethylmethanesulfonate) and random selection to improve production. A high producing strain (B9) was then selected for controlled production experiments of 15-Me-6-dEB, with and without added resin.

EXAMPLE 3

Precursor Compound

Racemic 2-methyl-3-hydroxyhexanoate-N-propionylcysteamine thioester ("Pr-SNPC"), was synthesized as described in Leaf et al., *J. Chem. Technol. Biotechnol.* 77, 1122-1126 (2002).

Pr-SNPC was used as the precursor compound for the biosynthesis of 15-Me-6-dEB by strain B9.

EXAMPLE 4

Media

Production cultures were prepared in SC-FM6-1 or SC-FM6-2 media. Shake flask medium pH was adjusted to pH 7.0 prior to sterilization by autoclaving (90 min at 121° C.). Bioreactor medium was prepared without HEPES buffer, autoclaved for 90 min at 121° C., and adjusted to pH 6.5 after cooling to 30° C. All media were supplemented with 10 mL/L of 50% (v/v) antifoam (Antifoam B, J. T. Baker, Phillipsburg, N.J.) as a post-sterilization addition. Seed culture medium was also supplemented with 50 mg/L thiostrepton (Calbiochem, La Jolla, Calif.) prepared in DMSO at 50 mg/mL. Strains were maintained as frozen cell banks prepared by adding glycerol (30% v/v final) to an exponentially growing culture (in seed medium) and freezing 1 mL aliquots at −85° C.

EXAMPLE 54

Cultivation

Primary seed cultures were established by inoculating 50 mL of SC-VM6-1 with a cell bank vial and cultivating for 3 days at 30° C. and 245 rpm. For shake flask studies, replicate flasks containing 35 mL of production medium were inoculated with 1.75 mL (5% v/v) of the primary seed culture. Flasks were incubated at 30° C. and 245 rpm for 6-8 days with 1 mL samples withdrawn as necessary and stored at −20° C. for analysis.

Bioreactor studies were performed in MD 5 L fermentors (B. Braun, Allentown, Pa.) with 4 L of production medium operated at 30° C., 0.75 VVM airflow, and 600-1200 rpm agitation. Samples were withdrawn as necessary and stored at −20° C. for later analysis. Dissolved oxygen concentration (percent of air saturation) and pH were monitored using autoclaveable electrodes (Mettler Toledo, Wilmington, Mass.). The dissolved oxygen was maintained above 50% by automatic control of agitation rate. Foaming was controlled by automatic addition of 50% (v/v) antifoam. The pH was controlled by automatic addition of 2.5 N sodium hydroxide or sulfuric acid. Bioreactors were inoculated with 200 mL secondary seed cultures prepared by sub-culturing 40 mL of primary seed into 500 mL of SC-VM6-1 and cultivating for 2 days.

For production of 6-dEB analogs, the diketide precursor was prepared by dissolving in DMSO (400 g/L final) and filter-sterilized with a 0.2 μm nylon membrane (VWR International, Brisbane, Calif.). Diketide was typically added at 2 g/L final concentration about 40-48 hrs after inoculation and maintained above 1 g/L as necessary with subsequent additions. For fermentations in presence of an adsorbent resin, XAD-16HP hydrophobic resin (Rohm & Haas, Philadelphia, Pa.) was sterilized in an equivalent amount of deionized water and added to a final concentration of 50 wet g/L immediately prior to diketide feeding.

EXAMPLE 5

Analysis

For analysis of product compound 15-Me-6-dEB and precursor compound Pr-SNPC, culture broth was diluted 1:1 with methanol (1:4 dilution with methanol for resin-containing cultures) and mixed for at least 1 hour. Samples were then centrifuged at 14,000×g for 5-10 min and the supernatant was analyzed by HPLC. Quantitation was performed using a Hewlett-Packard 1090 HPLC equipped with a diode array detector (DAD) and an Alltech 500 evaporative light scattering detector (ELSD). Supernatant was diluted as necessary and 4 μL was injected onto a guard column (4.6 mm×10 mm Inertsil ODS3-5 μm, Varian Analytical Instruments, Walnut Creek, Calif.) and main column (4.6 mm×50 mm Inertsil ODS3-5 μm, Varian Analytical Instruments). The assay method consisted of an extraction with 100% water for 2 min. bypassing the main column, a 6 min. gradient separation starting from 100% water and ending at 100% acetonitrile, followed by a 1 min. elution at 100% acetonitrile. 15-methyl-6-dEB eluted at 8.5 min. and was detected by the ELSD. Pr-SNPC eluted at 6.8 min. and was detected by UV absorbance at 250 nm. Quantitation was performed using a standard curve (100-500 mg/L 15-Me-6-dEB and 1 g/L Pr-SNPC) developed each time samples were analyzed. The 15-Me-6-dEB standards were prepared using material purified from fermentation broth.

EXAMPLE 5

Production with and Without Resin Present

Figure 1:
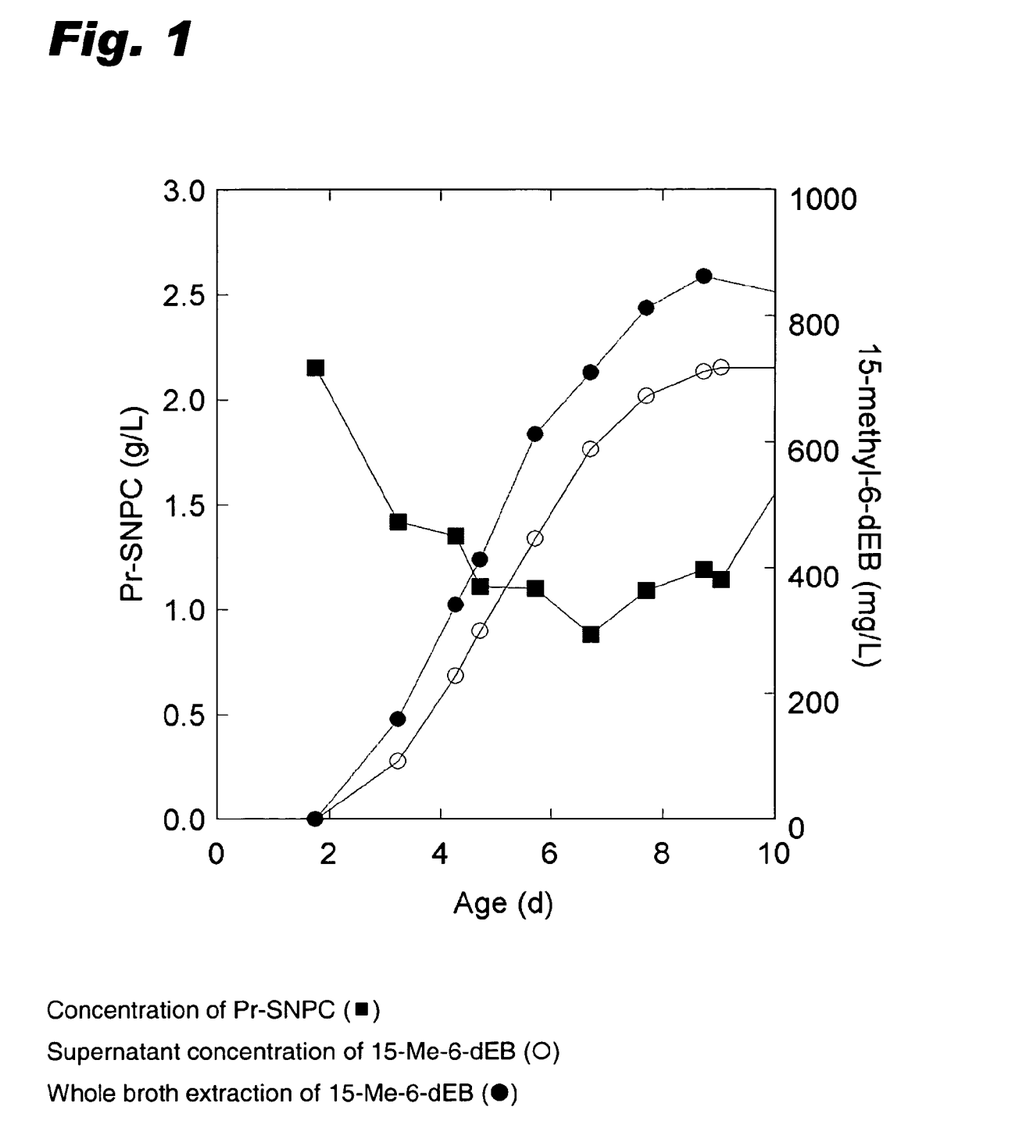
FIG. 1 shows product compound production and precursor compound concentration profiles for a representative fermentation run.

A preferred target concentration range for Pr-SNPC of approximately 1 to approximately 2 g/L (with a specific target of approximately 2 g/L) in the culture medium was selected, on the basis of empirical runs in 5 L fermenters. FIG. 1 depicts the 15-Me-6-dEB production and Pr-SNPC concentration profiles for a representative fermentation. In this fermentation Pr-SNPC was initially fed at 2 g/L at 40 hrs and then maintained above 1 g/L by subsequent additions to prevent precursor limitations. The fermentation scaled-up well from shake flask to fermenter and yielded 850 mg/L 15-Me-6-dEB after 9 days. This fermentation was analyzed for 15-Me-6-dEB in the clarified supernatant as well as from whole broth.

It was observed that 15-Me-6-dEB titers in the clarified supernatant were unstable and typically lower than titers in the whole broth as determined by a methanol extraction. It was hypothesized that 15-Me-6-dEB titers were above the solubility limit and that the titer decrease observed in clarified supernatant was due to precipitation of 15-methyl-6-dEB out of solution. Solubility issues would not affect whole broth extraction titers determinations since 15-methyl-6-dEB would be re-solubilized in 50% methanol.

Figure 2:
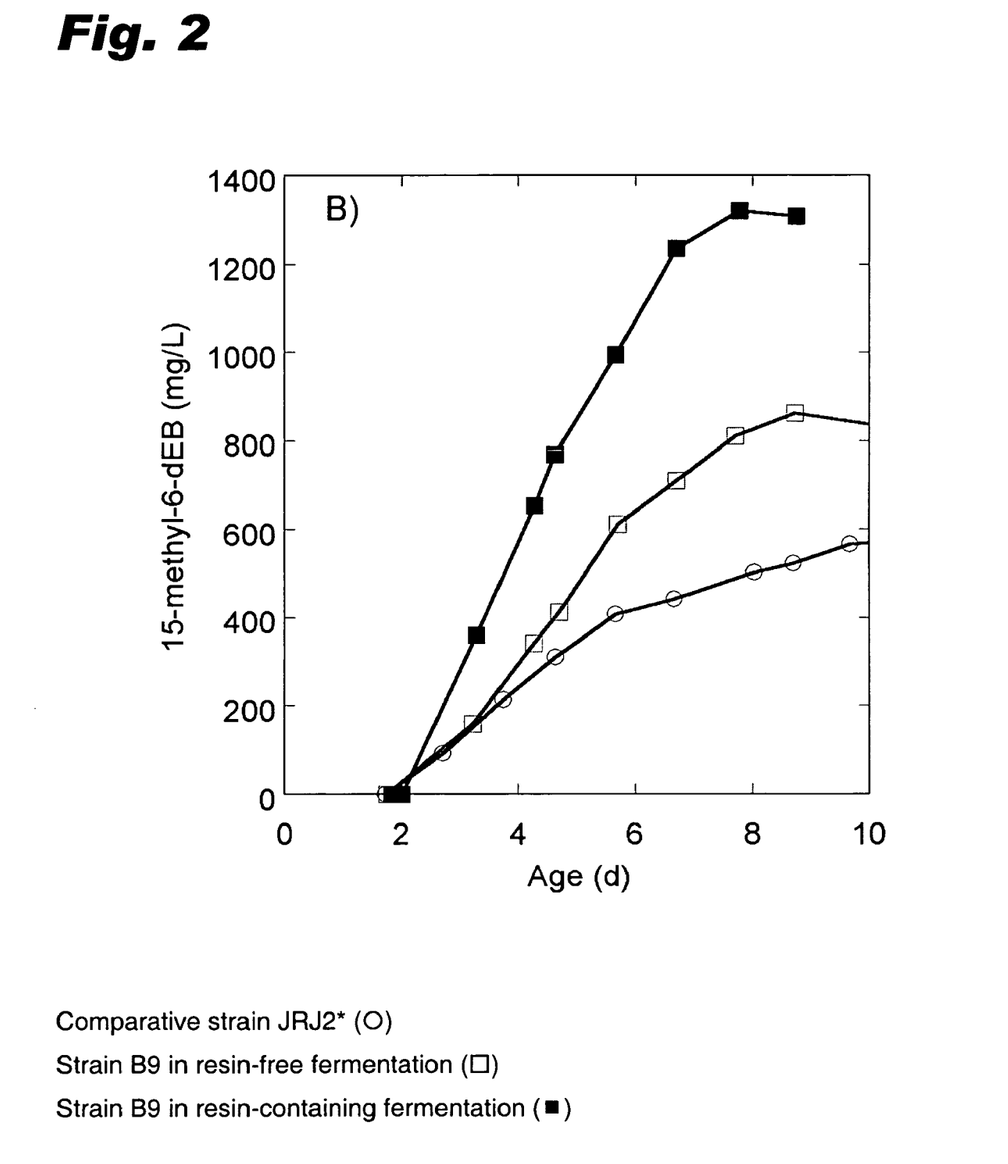
FIG. 2 shows how the presence of an adsorbent resin results in increased production of product compound.
Figure 3:
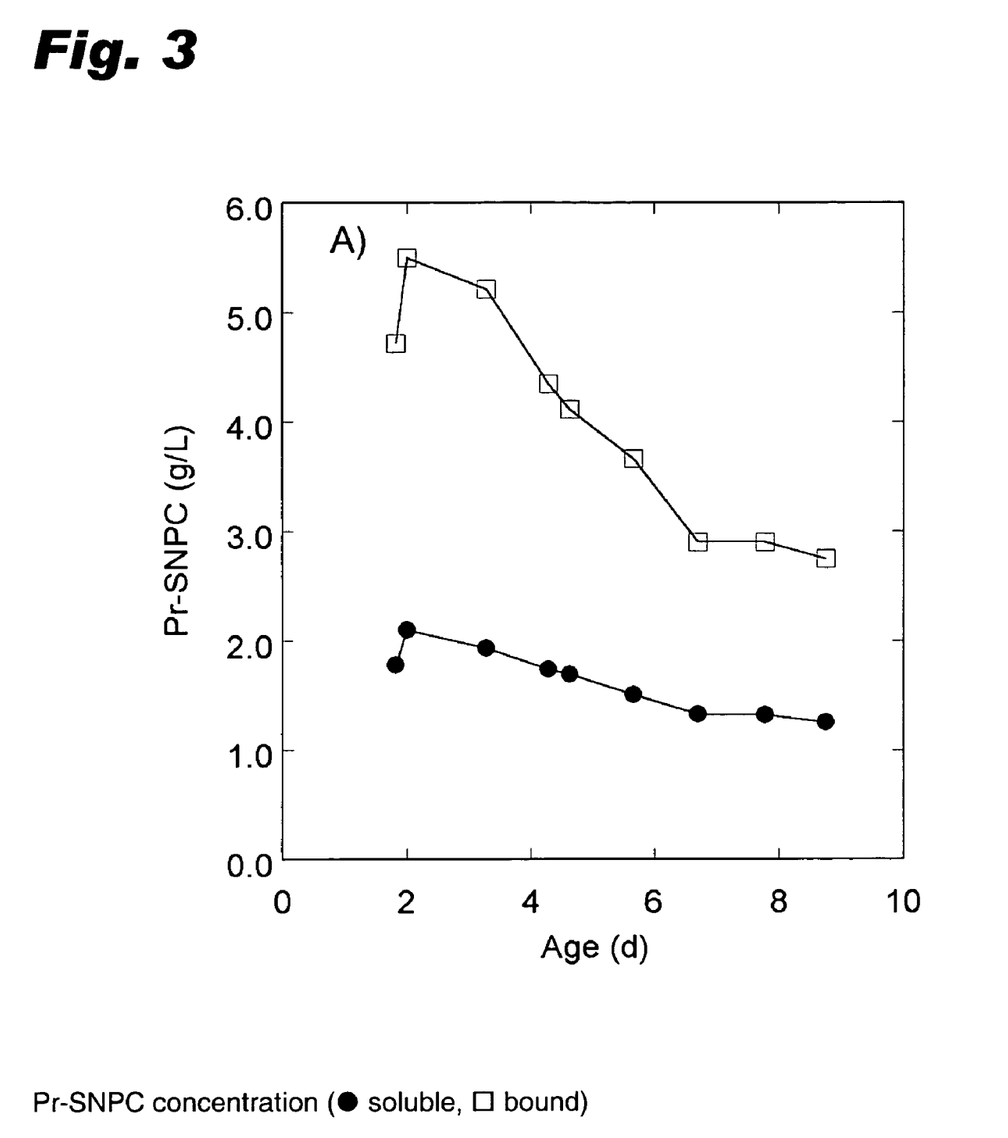
FIG. 3 shows how the adsorbent resin stabilizes the solution concentration of precursor compound.

Production runs were performed with and without XAD-16 resin present (50 g/L). Where XAD-16 resin was present, the total amount of Pr-SNPC added was to 7 g/L, corresponding to an unadsorbed, free Pr-SNPC concentration of approximately 2 g/L. FIG. 2 shows the productivity of 13-Me-6-dEB with and without resin present and also in comparison against a less productive, comparison strain. FIG. 3 shows how the presence of the XAD-16 resin stabilizes the solution concentration of Pr-SNPC, enabling fermentation to proceed for seven days without the need to add any Pr-SNPC.

Figure 4:
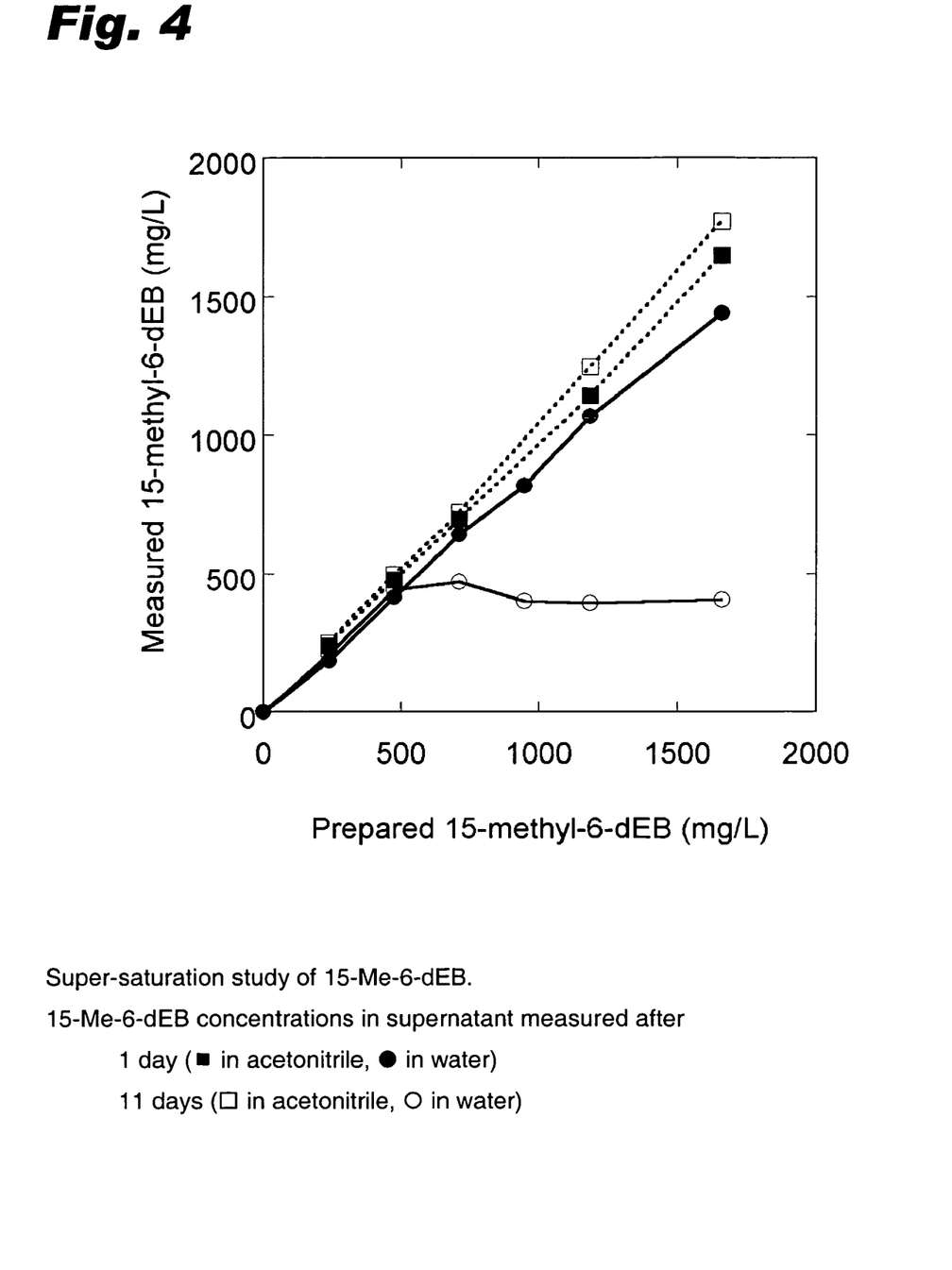
FIG. 4 shows the supersaturation curve for a product compound, 15-methyl-6-deoxyerythronolide B.

We have found that the presence of the resin provides another advantage. The product, 15-Me-6-dEB, has limited solubility in water, about 250 mg/L. Even though supersaturation occurs, in water the supersaturated concentration levels off at around 400 to 420 mg/L with time. FIG. 4 shows the supersaturation effect in water. Added hydrophobic resin sequesters the 15-Me-6-dEB and improves yield.

The foregoing detailed description of the invention includes passages that are chiefly or exclusively concerned with particular parts or aspects of the invention. They will also understand that, though the invention has been illustrated with one particular producing organism biosynthesizing one particular product compound from one particular precursor compound, the invention is generally applicable to other producing organisms producing other product compounds from other precursor compounds. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A method of making a polyketide, comprising the steps of:
    (a) providing a culture medium containing (i) a precursor compound for said polyketide, said precursor compound being selected from the group consisting of a starter unit and an extender unit, and (ii) a polyketide producing organism;
    (b) selecting a target concentration range for said precursor compound in said culture medium; and
    (c) culturing said polyketide producing organism in said culture medium to produce said polyketide, said culture medium being in contact with a resin that reversibly binds said precursor compound so that the concentration of un-adsorbed precursor compound in said culture medium is maintained within the target concentration range by the release of said precursor compound bound to the resin as said precursor compound is converted to said polyketide.

2. A method according to claim 1, wherein the target concentration range of said precursor compound is between 0.5 and 3.0 g/L.

3. A method according to claim 1, wherein said precursor compound is a starter unit.

4. A method according to claim 1, wherein said starter unit is a diketide.

5. A method according to claim 1, wherein said polyketide producing organism is a genetically engineered organism.

6. A method according to claim 1, wherein said polyketide producing organism is selected from the group consisting of *Streptomyces lividans, Streptomyces coelicolor, Saccharopolyspora erythraea, Streptomyces fradiae, Saccharomyces cerevisiae, Escherichia coli*, and *Myxococcus xanthus*.

7. A method according to claim 1, wherein said polyketide producing organism is *Streptomyces coelicolor*.

8. A method according to claim 1, wherein said polyketide producing organism is incapable of biosynthesizing said precursor compound.

9. A method according to claim 1, wherein said polyketide is a 6-dEB analog.

10. A method according to claim 9, wherein said polyketide is 15-methyl-6-dEB.

11. A method according to claim 1, wherein the resin comprises a non-ionic, hydrophobic resin.

12. A method according to claim 11, wherein the resin comprises polystyrene or a styrene-divinylbenzene copolymer.

* * * * *